United States Patent
Lakin

(10) Patent No.: US 7,621,962 B2
(45) Date of Patent: Nov. 24, 2009

(54) MODULAR RESURFACING PROSTHETIC

(75) Inventor: Ryan C Lakin, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 53 days.

(21) Appl. No.: 11/473,423

(22) Filed: Jun. 23, 2006

(65) Prior Publication Data

US 2006/0241779 A1 Oct. 26, 2006

Related U.S. Application Data

(63) Continuation of application No. 10/360,523, filed on Feb. 6, 2003, now abandoned.

(60) Provisional application No. 60/355,171, filed on Feb. 6, 2002.

(51) Int. Cl.
*A61F 2/32* (2006.01)
(52) U.S. Cl. .................................................. 623/22.15
(58) Field of Classification Search .............. 623/18.11, 623/22.11, 22.15, 22.21, 23.11, 23.12, 23.13, 623/23.14, 23.15, 23.26, 23.29, 23.3, 23.34, 623/23.35, 23.41, 23.44, 23.45
See application file for complete search history.

(56) References Cited

U.S. PATENT DOCUMENTS

| | | | |
|---|---|---|---|
| 2,934,065 A | 4/1960 | Townley | |
| 3,896,505 A | 7/1975 | Timmermans | |
| 4,095,591 A | 6/1978 | Graham, Jr. et al. | |
| 4,312,079 A * | 1/1982 | Dorre et al. | 623/23.12 |
| 4,715,860 A * | 12/1987 | Amstutz et al. | 623/22.33 |
| 4,728,330 A | 3/1988 | Comparetto | |
| 4,752,296 A | 6/1988 | Buechel et al. | |
| 4,795,473 A | 1/1989 | Grimes | |
| 4,892,546 A | 1/1990 | Kotz et al. | |
| 4,976,740 A * | 12/1990 | Kleiner | 623/23.14 |
| 5,176,681 A | 1/1993 | Lawes et al. | |
| 5,522,904 A | 6/1996 | Moran et al. | |
| 5,556,429 A * | 9/1996 | Felt | 128/898 |
| 5,766,263 A | 6/1998 | Grundei et al. | |
| 5,800,557 A | 9/1998 | Elhami | |
| 5,871,547 A | 2/1999 | Abouaf et al. | |
| 5,980,575 A | 11/1999 | Albrektsson et al. | |
| 6,096,084 A | 8/2000 | Townley | |
| 6,129,764 A | 10/2000 | Servidio | |
| 6,231,611 B1 * | 5/2001 | Mosseri | 623/22.12 |
| 6,508,841 B2 | 1/2003 | Martin et al. | |
| 6,520,964 B2 | 2/2003 | Tallarida et al. | |
| 6,607,561 B2 * | 8/2003 | Brannon | 623/23.11 |
| 6,610,067 B2 | 8/2003 | Tallarida et al. | |
| 6,679,917 B2 | 1/2004 | Ek | |

FOREIGN PATENT DOCUMENTS

WO WO 97/47257 * 12/1997

* cited by examiner

*Primary Examiner*—Eduardo C Robert
*Assistant Examiner*—David Comstock
(74) *Attorney, Agent, or Firm*—Harness, Dickey

(57) ABSTRACT

Femoral head modular resurfacing systems are described. The systems primarily include a head component and a stem component. The configuration of the head component and stem components allow for minimum invasiveness into the femur head region, thus conserving greater amounts of bone tissue than would be possible with conventional hip replacement systems. The systems also provide for various angles and offsets to be achieved between the systems and the femur head. The systems are useful in partial hip replacement procedures, as well as total hip replacement procedures, in which case an optional acetabular component would also be employed.

20 Claims, 10 Drawing Sheets

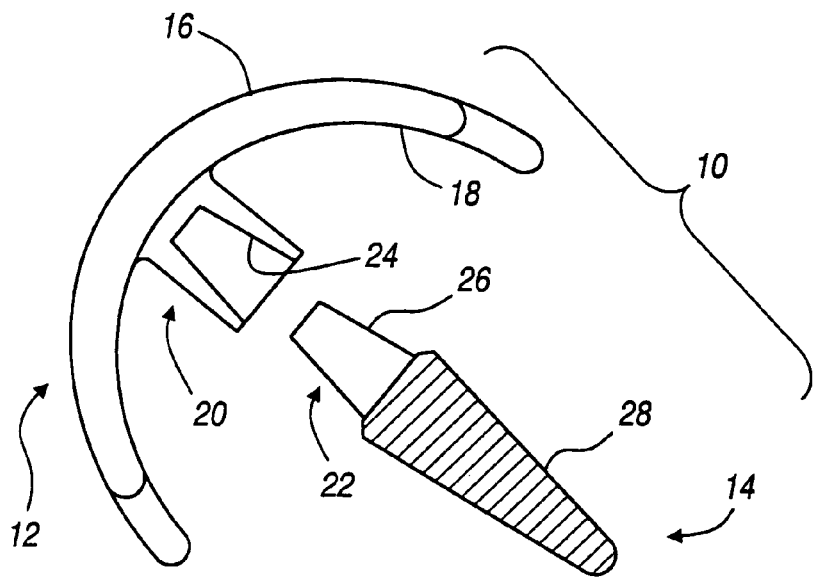
FIG. 1
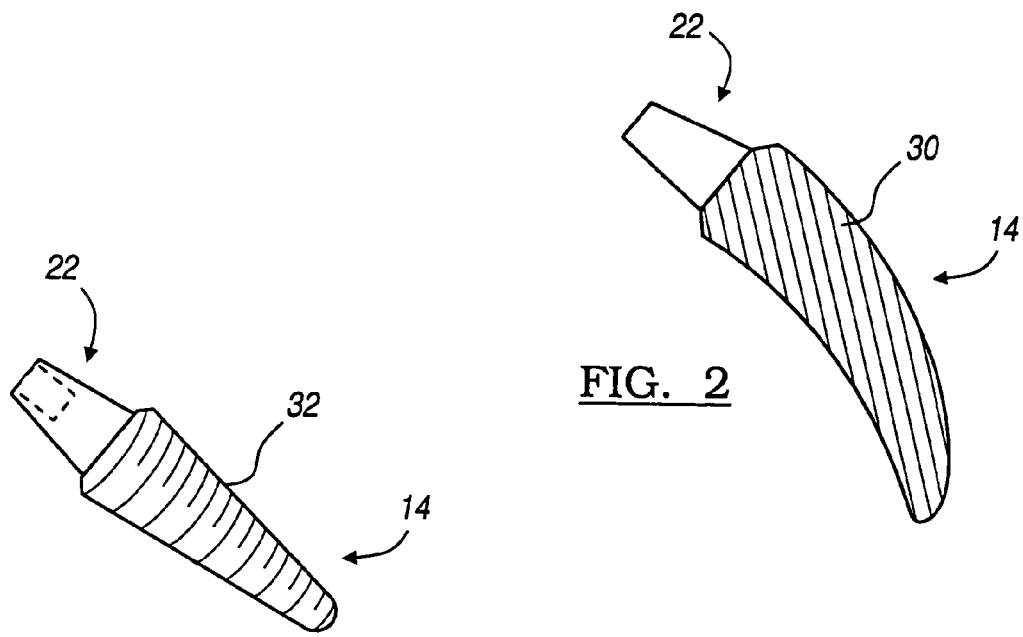
FIG. 2
FIG. 3

MODULAR RESURFACING PROSTHETIC

CROSS-REFERENCE TO RELATED APPLICATIONS

This application is a continuation application of U.S. patent application Ser. No. 10/360,523 filed on Feb. 6, 2003, which claims the benefit of U.S. Provisional Application No. 60/355,171 filed on Feb. 6, 2002. The disclosures of the above applications are incorporated herein by reference.

FILED OF THE INVENTION

The present invention relates generally to prosthetic components useful for hip replacement procedures, and more particularly to systems, and methods of using same, for the minimally invasive resurfacing of diseased or defective portions of the femoral head. The system primarily includes modular femoral head and stem components that permit minimal amounts of the femoral head to be resected during hip joint replacement procedures. The system also includes an optional acetabular component that properly articulates with the femoral head component.

BACKGROUND OF THE INVENTION

A natural hip joint may undergo degenerative changes due to a variety of etiologies. When these degenerative changes become so far advanced and irreversible, it may ultimately become necessary to replace a natural hip joint with a prosthetic hip. When implantation of such a hip joint prosthesis becomes necessary, the head of the natural femur is first resected and a cavity is created (e.g., by reaming and broaching) within the intermedullary canal of the host femur for accepting the hip prosthesis, typically referred to as a femoral insert. The femoral insert may be inserted and supported within the host femur by cementing the femoral insert within the host femur. Alternatively, the femoral insert may be impacted into the host femur so that it is snugly fit and supported by the host femur.

Due to any number of reasons, however, a small portion of patients that undergo such orthopedic surgical procedures may require subsequent revision surgery to replace the hip prosthesis with a new prosthetic device generally referred to as a revision prosthesis. Because conventional hip replacement procedures typically remove significant amount of bone tissue from the area surrounding the proximal intermedullary canal, there are significant problems associated with securing the revision prosthesis to the remaining femoral structure.

Accordingly, there has been increasing reluctance on the part of orthopedic surgeons to remove the entire femur head as well as to remove any significant amounts of bone tissue in the proximal intramedullary canal during hip joint replacement surgery. This is especially true with respect to patients that have only slight to moderate bone tissue damage on the surface of the femur head (e.g., caused by vascular necrosis or osteonecrosis). In these cases, the limited amount of bone tissue damage on the surface of the femur head would appear to contraindicate the necessity of removing the entire femur head in order to accommodate a conventional femoral insert.

This need has led to the development of femoral resurfacing components that require only that a portion of the femur head be resected, rather than the entire femur head. Presently, all currently available femoral resurfacing components are comprised of a single, unitary piece and either have a relatively short or relatively long, straight post to follow down the femoral neck. However, a major disadvantage of these components is that they significantly limit the versatility of femoral neck options and degree of offset, they are susceptible to early loosening and femoral neck fractures, and they require substantial rehabilitation periods similar to traditional total joint replacement techniques.

Therefore, there exists a need for femoral resurfacing systems, and methods of using same, for minimizing the amount of bone tissue that needs to be removed from the proximal femur, such as the femur head and proximal intramedullary canal, during a hip replacement procedure and simultaneously allows a number of different configurations, angles, and offsets to be easily and inexpensively achieved.

SUMMARY OF THE INVENTION

In accordance with the general teachings of the present invention, systems, and methods of using same, are provided for a minimally invasive partial or total hip replacement. The systems minimize the amount of bone tissue that is required to be removed from the femoral head region, thus conserving bone tissue for any future revision procedures. The system primarily includes a head component and a stem component for partial resurfacings (e.g., only the surface of the femur head is removed) and an optional acetabular component for total resurfacings (e.g., both the surface of the femur head and the surface of the acetabulum are removed). The systems may be secured in place by press fitting, cementing, or through the use of various mechanical fasteners.

A more complete appreciation of the present invention and its scope can be obtained from the following detailed description of the invention and the drawings.

BRIEF DESCRIPTION OF THE DRAWINGS

The present invention will become more fully understood from the detailed description and the accompanying drawings, wherein:

FIG. 1 illustrates an exploded view of a femoral head modular resurfacing system, in accordance with one embodiment of the present invention;

FIG. 2 illustrates a perspective view of a stem component, in accordance with one embodiment of the present invention;

FIG. 3 illustrates a perspective view of another stem component, in accordance with one embodiment of the present invention;

The same reference numerals refer to the same parts throughout the various Figures.

DETAILED DESCRIPTION OF THE INVENTION

Figure 4:
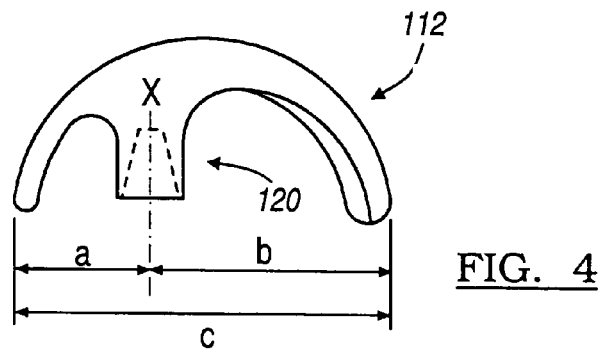
FIG. 4 illustrates an elevational view of an alternative head component, in accordance with an alternative embodiment of the present invention.

In accordance with a first embodiment of the present invention, a femoral head modular resurfacing system generally denoted as 10 is shown in FIG. 1. The system 10 primarily includes a head component 12 and a stem component 14. The intended objective of the system 10 is to provide for a head resurfacing (either partial or full) component that will allow for a variety of femoral neck segments to either act as a hemi-arthroplasty (removal of the surface of the femur head) or a total resurfacing component (removal of both the surface of femur head as well as the surface of the acetabulum).

The head component 12 can be comprised of any number of biocompatible materials, such as but not limited to titanium, cobalt chrome, stainless steel, ceramics or any other material that can serve as a bearing surface. The head component 12 can articulate either on the natural acetabulum or on an acetabular component (not shown) such as one made of cobalt chrome or any other suitable biocompatible material in order to provide for a metal-metal articulation.

The head component 12 is shown as being substantially hemispherical in shape, although the present invention envisions modifications to the shape shown. For example, the head component 12 can be either a full, greater than full, or partial hemisphere. The head component 12 preferably includes a substantially hemispherical outer articulating surface 16 and a substantially hemispherical inner bearing surface 18 which is intended to bear or abut against the resected surface of the femur head.

A connection member 20 extends outwardly from the inner surface 18 and is intended to cooperate with a complementary connection member 22 on the stem component 14. Although the connection member 20 is shown as comprising a female Morse taper 24, it is also envisioned that other types of connection configurations may be employed. For example, a male Morse taper may be used as well. Furthermore, threaded configurations may also be used. Additionally, although the connection member 22 is shown as comprising a male Morse taper 26, it is also envisioned that other types of connection configurations may be employed. For example, a female Morse taper may be used as well. Furthermore, threaded configurations may also be used.

Accordingly, the locking mechanism between the two components can be a taper (either self-locking or non-self-locking) as previously described, a screw mechanism, or any other locking mechanism sound enough to hold the two components together without any appreciable movement.

The stem component 14 can be configured in any number of shapes (e.g., curved (see FIG. 2), tapered, conical (see FIG. 3), cylindrical, radial, fluted, and so forth). The surface finish of the stem component 14 can be smooth, plasma spray 28, porous coating 30 (see FIG. 2), threaded 32 (see FIG. 3), polished, grit blasted, and so forth). The material comprising the stem component 14 can be any biocompatible material such as but not limited to titanium, cobalt chrome, stainless steel, ceramics, and so forth.

The cross-sectional profile of the stem component 14 may comprise many different shapes, and can either be used in a press-fit or cemented application for implantation. The stem component 14 would typically be placed into the femoral neck either with or without entering into the diaphyseal femoral canal.

Figure 5:
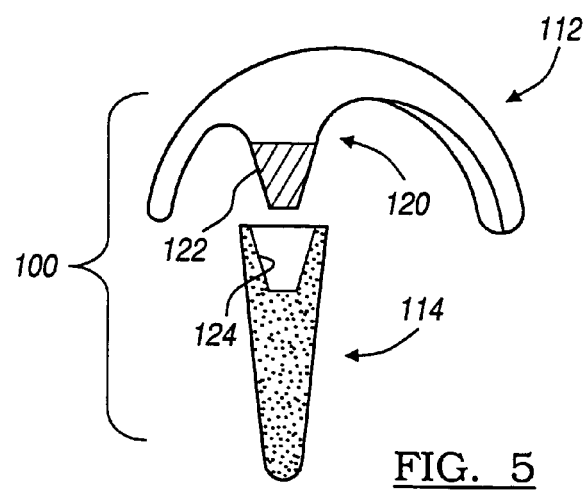
FIG. 5 illustrates an exploded elevational view of an alternative femoral head modular resurfacing system, in accordance with an alternative embodiment of the present invention.
Figure 6:
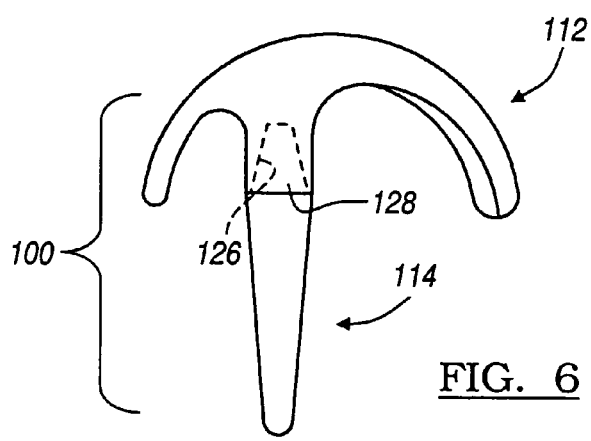
FIG. 6 illustrates an elevational view of another alternative femoral head modular resurfacing system, in accordance with an alternative embodiment of the present invention.

Referring to FIGS. 4-6, the head component 112 could be offset either by placing the connection member 120 (e.g., taper or whatever locking mechanism is employed) offset to the pole or by using an offset stem component 114. In FIG. 4, the distance "a" from one edge of the head component 112 to the center axis X of the connection member 120 is less than the distance "b" from the other edge of the head component 112 to the center axis X of the connection member 120. The total distance between the outer edges of the head component 112 is denoted as "c". Accordingly, the offset feature requires that length "a" does not equal length "b". The precise nature by which the two components are connected in the offset mode is not thought to be critical. Thus, in FIG. 5, the system 100 includes a head component 112 that is provided with a tapered male member 122 which is intended to mate with a tapered female member 124 on the stem component 114. Conversely, in FIG. 6, the system 100 includes a head component 112 that is provided with a tapered female member 126 which is intended to mate with a tapered male member 128 on the stem component 114.

This alternative embodiment of the present invention will allow a surgeon to pick a variety of stem components to match the femoral canal and indications of the particular component. The stem component can be matched with a full or partial head component and provide for full or partial coverage in particular areas of the femoral head by utilizing the offset feature.

Figure 7:
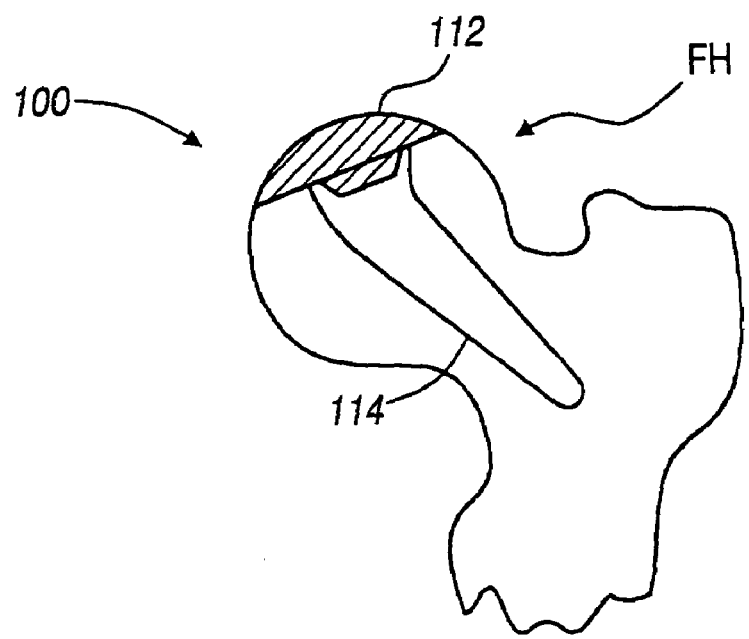
FIG. 7 illustrates a partial sectional view of an offset femoral head modular resurfacing system implanted into the femur head region of a patient, in accordance with one embodiment of the present invention.

Referring to FIG. 7, there is shown the offset system 100 implanted into the femur head region FH of a patient. The surface of the femur head is first resected only to the degree necessary to permit the implantation of the respective components. A bore is then provided from the resected surface of the femur head downwardly through the remaining portion of the femur head. The stem component 114 is then implanted into the bore provided in the proximal portion of the femur and can be held in place by bone cement or any other suitable means. The head component 112 bears against the resected surface of the femur head and is then fastened to the stem component 114.

Figure 8:
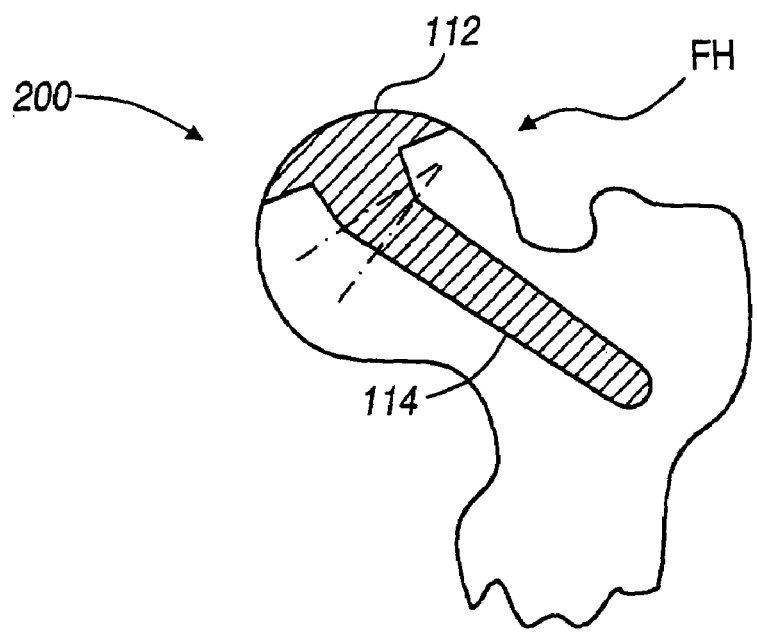
FIG. 8 illustrates a partial sectional view of an alternative offset femoral head modular resurfacing system implanted into the femur head region of a patient, in accordance with an alternative embodiment of the present invention.

Referring to FIG. 8, there is shown an offset system 200 implanted into the femur head region FH of a patient, in the same manner as described above. However, in this view, the head component 112 and the stem component 114 consist of a single, unitary system 200, as opposed to individual discrete components.

Figure 9:
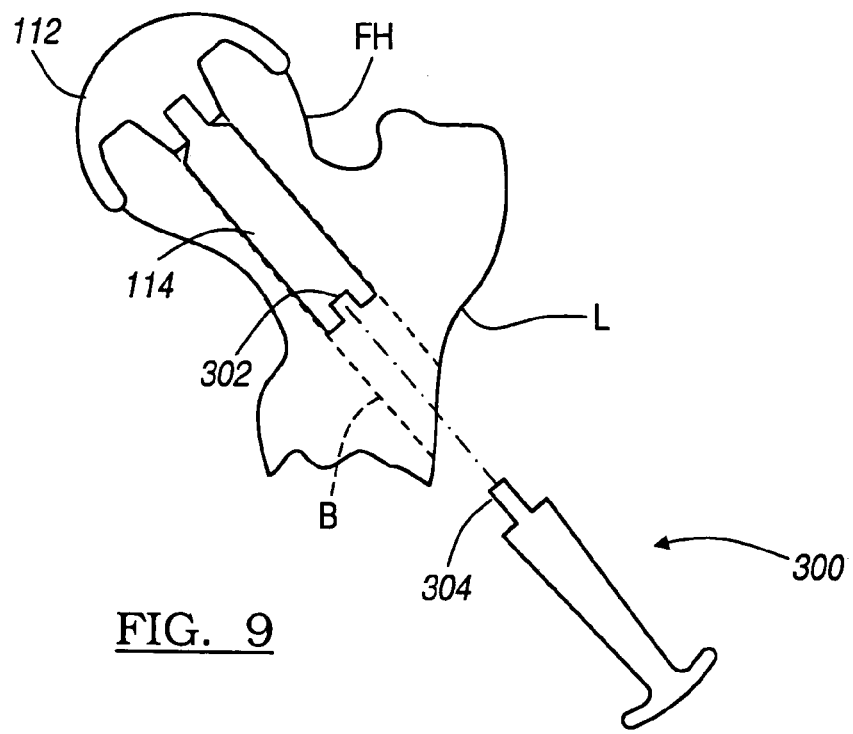
FIG. 9 illustrates a partial sectional view of a fastening member for use with an alternative offset femoral head modular resurfacing system implanted into the femur head region of a patient, in accordance with an alternative embodiment of the present invention.

If a non-cemented option is desired, a fastening member 300 can be provided on the lateral side L of the femur in order to secure the stem component 114 in place, as shown in FIG. 9. Of course, a bore B will have to be provided on the lateral side L of the femur so that the fastening member 300 can access the stem component 114. Additionally, a cooperating fastening member 302 must also be provided on the distal surface of the stem component 114 so as to be able to engage the fastening surface 304 of the fastening member 300.

Figure 10:
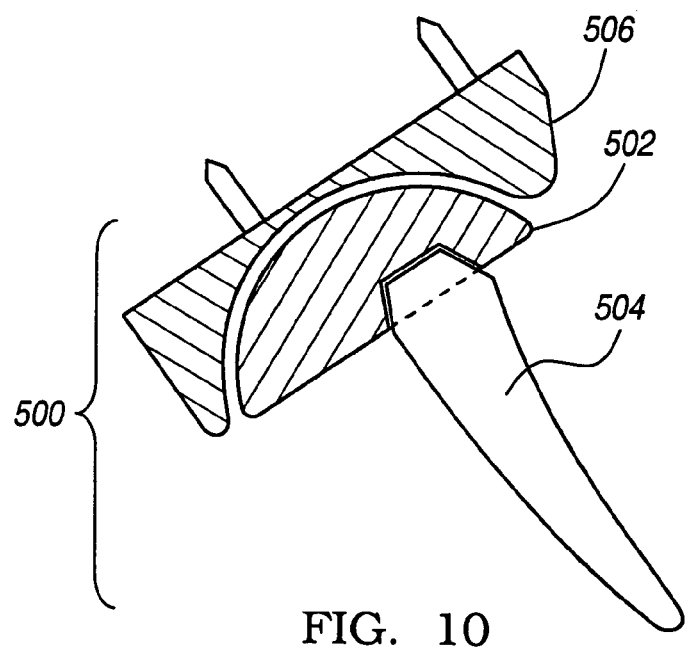
FIG. 10 illustrates an elevational view of a minimally invasive total hip replacement system, in accordance with an alternative embodiment of the present invention.

In accordance with a second embodiment of the present invention, a minimally invasive total hip replacement system generally denoted as 500 is shown in FIG. 10. The system 500 primarily includes a head component 502, a stem component 504, and an acetabular component 506 that is intended to properly articulate with the head component 502.

The intended objective of the second embodiment of the present invention is to provide a minimally invasive total hip replacement system (i.e., both femur head and acetabulum resurfacing) with either metal-metal or ceramic-ceramic articulation that would allow for implantation with minimal bone tissue removal.

The head component 502 and the stem component 504 are similarly to the previously described components in terms of shape, configuration, materials, and so forth. The acetabular component 506 would preferably utilize optimal material and precision manufacturing tolerances for use as a metal-metal bearing. The acetabular component 506 would preferably be a press-fit component with some type of texturing on the backside to promote bone in-growth/on-growth and may or may not have a means for supplemental fixation. The typical material would be cobalt chrome, although other biocompatible materials may be used as well.

The design of the acetabular component 506 is such that it requires removing a section of the acetabulum as compared to taking a spherical reamer to remove the diseased or defective area. Referring to FIG. 11, the sections are removed from the typical wear region WRA of the acetabulum where there is easy access to the pelvis. The cuts are made to match the implant that would have a spherical region for the bearing surface and the backside geometry would be the same as the cuts made in the pelvis. The resection would most likely occur in the superior-posterior region of the pelvis. The backside geometry of the acetabular component 506 could comprise both spherical and flat portions.

The preparation of the femoral head FH is through flat cuts or via a spherical type of reamer to remove the diseased or defective portion WRF of the femur head FH. Only a minimal amount of bone tissue is removed with the systems of the present invention, as shown in FIGS. 11a-11c.

Figure 11A:
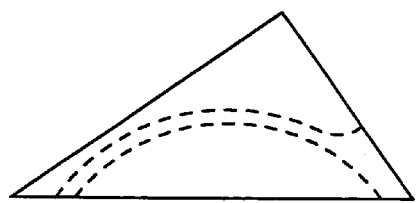
FIGS. 11a-11c depict various views of examples of resections according to the teachings of the present invention.
Figure 11B:
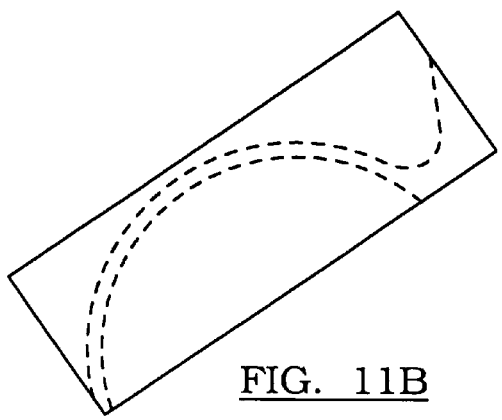
Figure 11C:
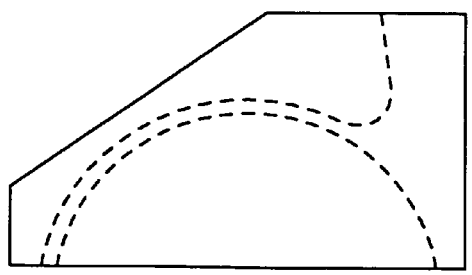

FIGS. 11a-11c represent views of example resections of hips according to the teaching of the present invention. In each of the figures, the hip is distracted the minimal amount necessary to position the cutting tools so as to remove the minimal amount of tissue needed. As can be seen, generally straight cuts can be used to resect both the acetabulum and the humeral component.

The implantation of this system is accomplished without dislocating the hip joint. Space is created within the joint by making both the acetabular and femoral head resection cuts. Final preparation is then completed utilizing a combination of reamers and cutting blades. The reamers are then activated by using a power handle introduced through the same incision.

Figure 12A:
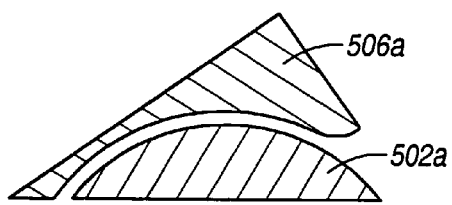
FIGS. 12a-12c depict modular components corresponding to the resections shown in FIGS. 11a-11c.
Figure 12B:
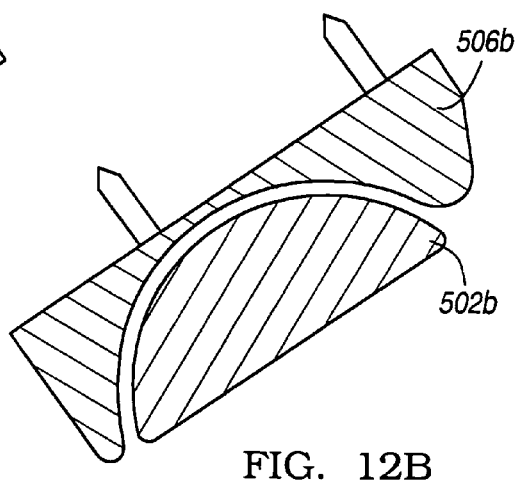
Figure 12C:
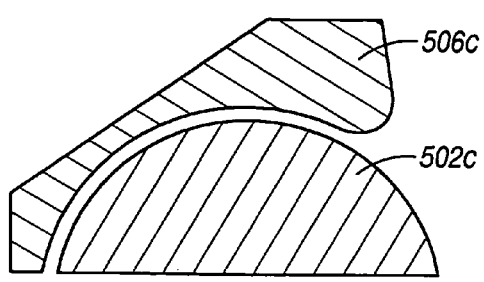

FIGS. 12a-12c represent portions of the implant according to the resection's shown in FIGS. 11a-11c. In each figure, a partial humeral head components 502a-c is shown. As is shown in FIGS. 1-10, these humeral components can be coupled to with the humerus utilizing various fixation techniques, for example stems, screws, and bone cement.

Further shown the acetabular components 506a-c which replace all or a portion of the acetabular cup. It is envisioned that each of the acetabular component will be fixed to the resected acetabulum by way of bone screws, pegs and or bone cement.

Figure 19:
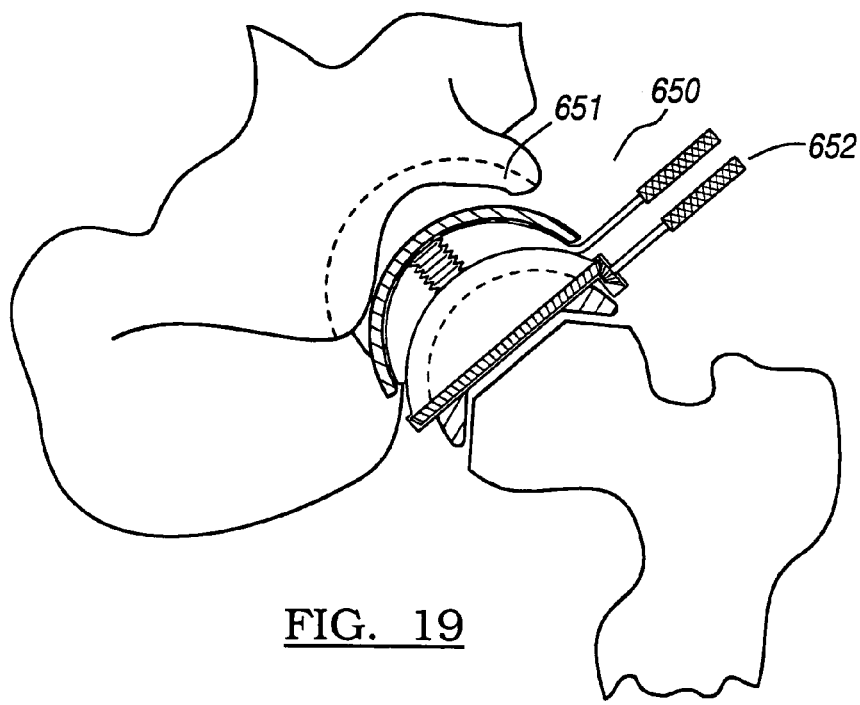
FIGS. 19 and 20 depict the method of implanting the embodiments of the present invention.
Figure 20:
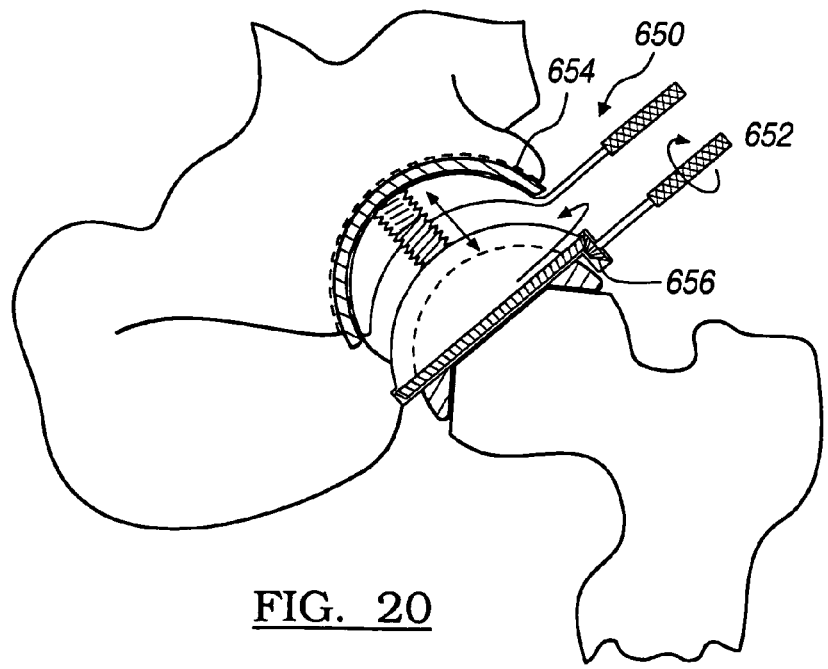

The system components are then inserted together utilizing instrumentation to orient and impact the respective components. The instrument is mechanically separated through a screw (or similar) mechanism thus applying loads to both the femoral and acetabular component. The implanted system 500 is shown in FIGS. 19-20.

This second embodiment of the present invention allows a total joint prosthesis that is completed without dislocating the hip joint and has the benefits of a metal-metal articulation. The hip joint does not need to be distracted because of the bone cuts creating the space for preparation. The implants can be implanted through one incision. This will allow a surgeon to pick from a variety of head components and acetabular components to suit the specific needs of the patient.

Figure 13A:
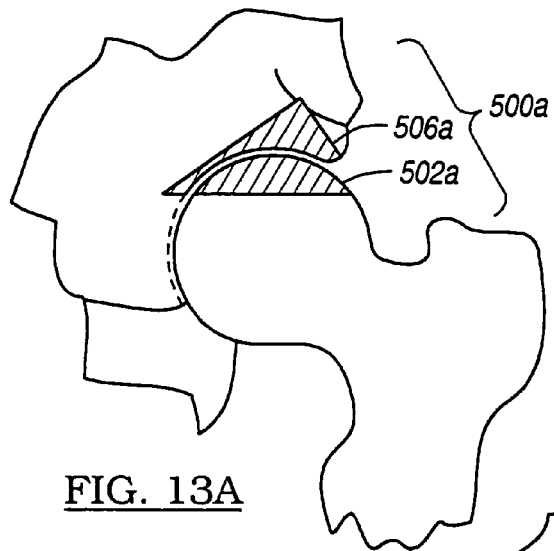
FIGS. 13a-13d illustrate cross sectional views of the minimally invasive, compliant fixation, total hip replacement system, in accordance with the embodiments depicted in FIGS. 12a-12c.
Figure 13B:
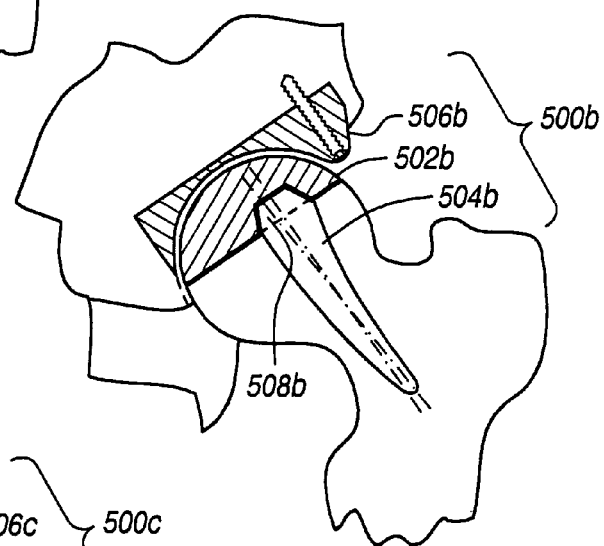
Figure 13C:
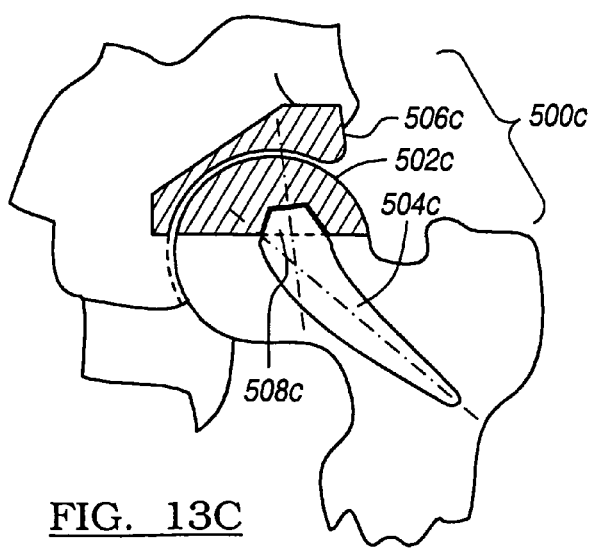
Figure 13D:
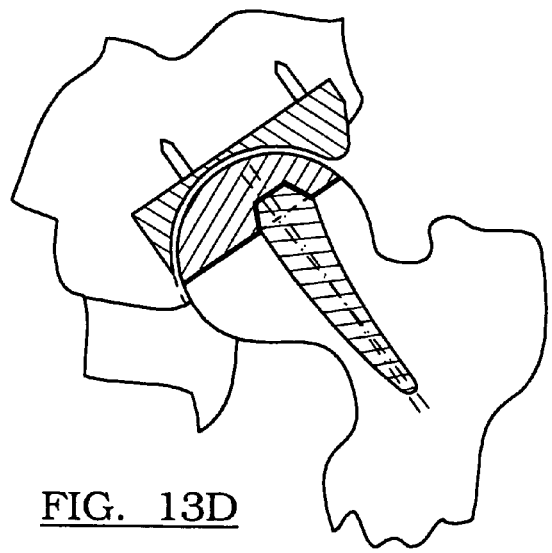

FIGS. 13a-13c represent another embodiment of the present invention. A minimally invasive, compliant fixation, modular metal/metal total hip replacement system generally denoted as 500a-c are shown in FIGS. 12a-12c. The system 500a-c primarily include a head component 502a-c, a stem component 504a-c, an acetabular component 506a-c that are intended to properly articulate with the head component 502a-c, and a fastening member 608a-c which fastens the head component 502 to the stem component 504.

The objective of this embodiment of the present invention is to provide the ability to perform a hemi-resurfacing (femoral head only) or total resurfacing (femoral head and acetabulum to provide metal-metal articulation) that would allow for a variety of head options and allow a minimally invasive preparation and implantation with minimal bone tissue removal.

Figure 14:
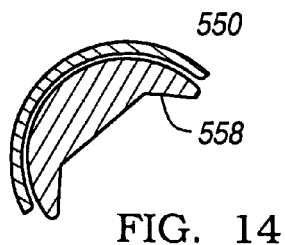
FIG. 14 illustrates a side view of an alternative embodiment of the present invention.
Figure 15:
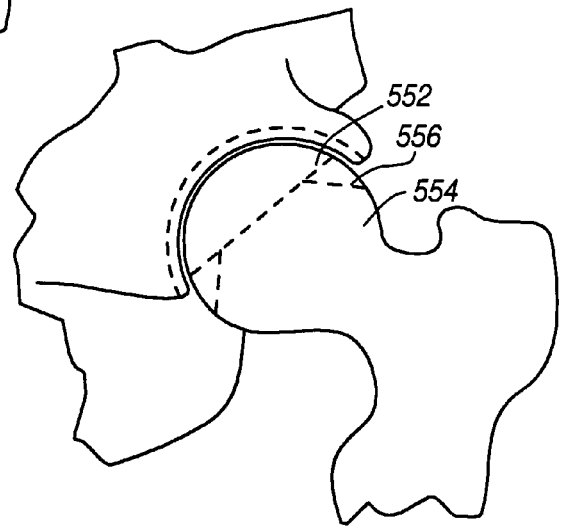
FIG. 15 depicts the resection of the humeral components necessary to insert the embodiment shown in FIG. 14.
Figure 16:
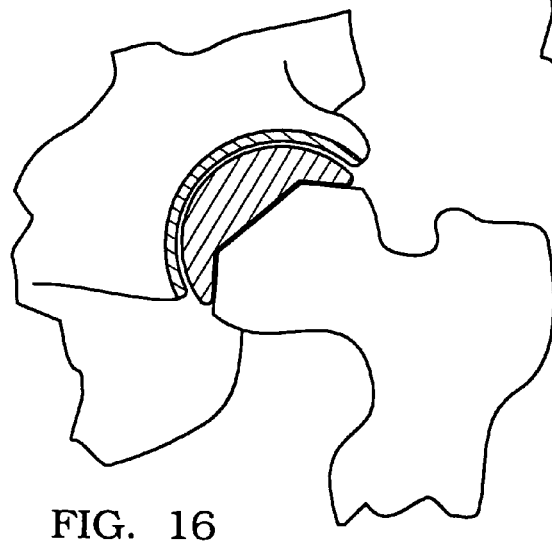
FIG. 16 illustrates a cross sectional view of the minimally invasive, compliant fixation, total hip replacement system, in accordance with the embodiments depicted in FIG. 14.
Figure 17:
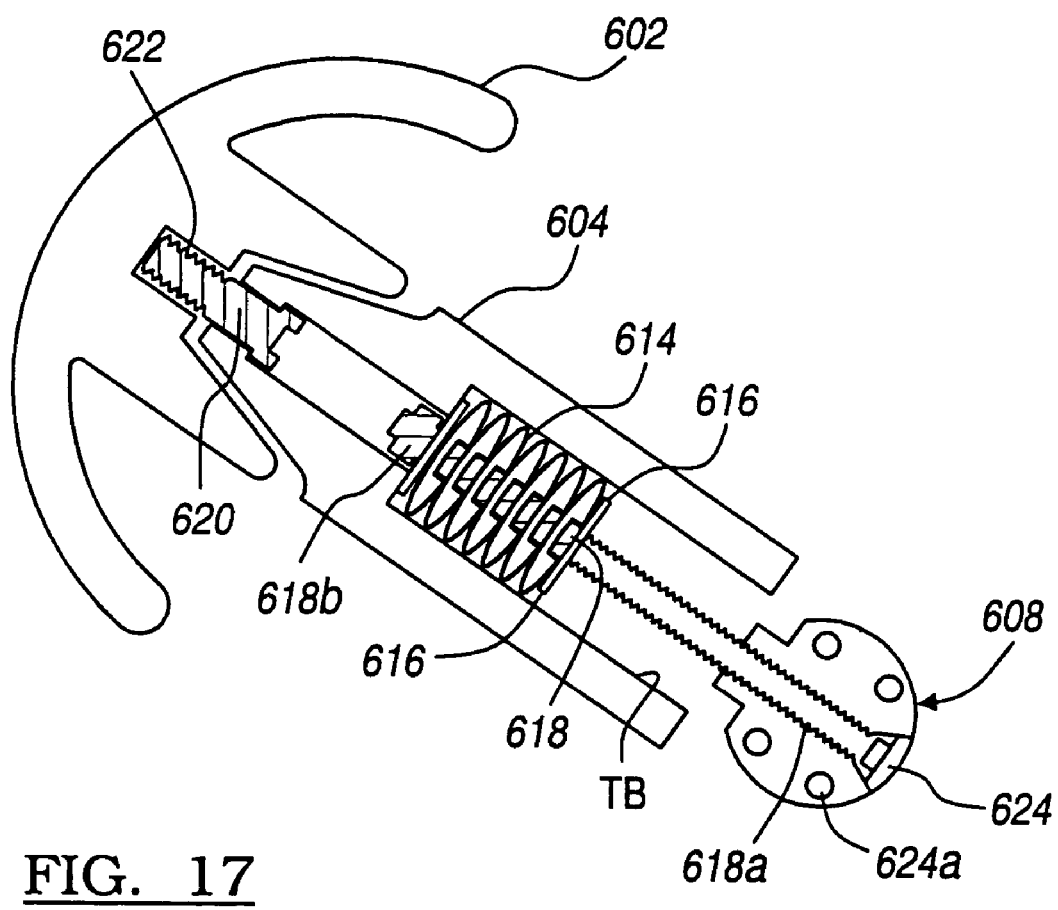
FIGS. 17 and 18 illustrate a partial elevational view of the system in accordance with an alternative embodiment of the present invention.
Figure 18:
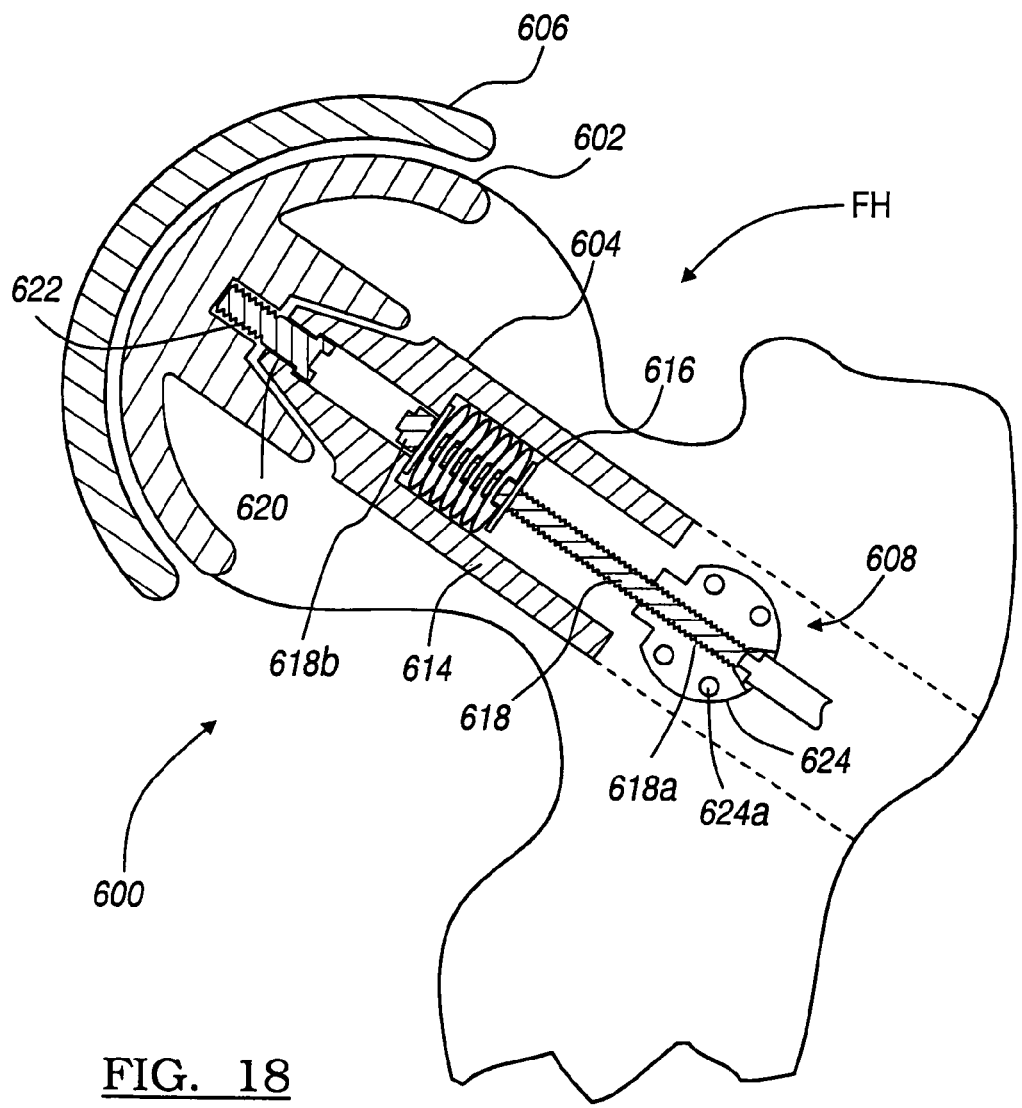

FIGS. 14-16 represent an alternative embodiment of the present invention. The system 550 couples to a spherically resected acetabulum. Also shown is the resected head portion. As can be seen, an initial flat resection 552 is made to humeral head 554. Additionally, a conical surface 556 is formed using a rotating conical reamer. These resected surfaces 553 and 556 mate to a coupling surface 558 of the humeral member 560.o As depicted in FIGS. 17 and 18, the components of the system 600 are similar to those depicted in connection with system 500 of the second embodiment, in terms of general shape, configuration, and materials. However, it should be noted that the stem component 604 and the fastening member 608 of the system 600 have been substantially modified, as will be described herein.

The fastening member 608 is intended to fasten the head component 602 to the stem component 604. For example, the fastening member 608 can be provided with a threaded distal portion 610 that cooperates with a threaded female surface 612 located on the undersurface of the head component 602. Of course, a throughbore TB must be provided in the stem component 604 to receive the fastening member 608. By rotating the fastening member 608 in the appropriate direction, the threaded distal portion 610 will eventually engage the threaded female surface 612 so as to firmly hold the respective components tightly together.

Alternatively, instead of using a simple screw assembly, a compression assembly may be used, as shown in FIG. 18. The view shown in FIG. 17 is the fully tightened and secured positioned. The throughbore TB of the stem component 604 contains a stack of washer elements 614, retaining ring 616 and compression bolt 618 are contained. The set screw 620 is tightened into the fastening member 622 of the head component 602 utilizing the compression bolt 618 that has the opposite mechanism as the set screw 620. The washer stack 614 is kept in place by the use of retaining ring 616. The threaded portion 618A of the compression bolt 618 extends outside of the stem component 604 with its head 618B contained in the stem component 604 above the washer stack 614. The anchor plug 624 is preferably made of a biocompatable material and contains a throughbore through the center which is threaded to connect to the threaded portion 618A of the compression bolt 618. The anchor plug 624 preferably contains holes 624A to which one or more cross pins (not shown) are placed to secure the anchor plug 624 in place.

The system 600 is loaded when the compression bolt 618 is threaded into the anchor plug 624. As a result, the washer stack 614 is compressed, thus creating a load that tries to pull the anchor plug 624 and the stem component 604 together, thus placing load onto the femoral head and cross pins (not shown). This load creates stimulation to the femoral head, thus promoting bone in-growth.

Referring to FIG. 18, there is shown the system 600 implanted into the femur head region FH of a patient. The system 600 is shown in its relaxed or loose state, in that the compression bolt 618 has not engaged the set screw 620.

The implantation of the system 600 is accomplished in substantially the same manner as previously described for system 500.

FIGS. 19-20 represent implantation of the system according to one embodiment of the present invention. While FIGS. 19-20 depict the implant of the prosthetic according to FIG. 14, it should be understood that the same method can be used to implant any of the implants shown herein.

As previously described, the joint being resurfaced, is a distracted an amount necessary for the proper resection of the articulating surfaces. Once the resected, the humeral and acetabular components are inserted between the resected surfaces. Furthermore, should bone cement be necessary, it should be inserted between the components and the resected surface prior to the coupling of the component members to the resected surface.

After the humeral and femoral component has been inserted into the joint, and insertion tool 650 is inserted between the acetabular and humeral components. The components are then set onto the resected surface 651 by applying a pressure and/or forces from the insertion tool 650.

As best can be seen in FIG. 18, rotational forces can be applied to the handle 652 which are translated into separation all forces between top and bottom members 654 and 656. It is envisioned that a mechanism, which can apply the necessary loading onto the humeral or acetabular components can be used.

The foregoing description is considered illustrative only of the principles of the invention. Furthermore, because numerous modifications and changes will readily occur to those skilled in the art, it is not desired to limit the invention to the exact construction and process shown as described above. Accordingly, all suitable modifications and equivalents that may be resorted to that fall within the scope of the invention.

What is claimed is:

1. A method for implanting a joint prosthesis into a hip joint, the method comprising:
   removing only a first portion of a femoral head bearing surface while the joint is in a non-distracted position;
   removing only a second portion of an acetabulum bearing surface while the joint is in a non-distracted position;
   implanting a first prosthetic device onto the femoral head to replace the first portion, while the joint is in a non-distracted position, the first prosthetic being positioned to place a first articulating bearing surface flush with a non-removed articulating bearing portion of the head; and
   implanting a second prosthetic device into the acetabulum to replace the second portion, while the joint is in a non-distracted position, the second prosthetic being positioned to place a second bearing surface flush with a non-removed bearing portion of the acetabulum.

2. The method according to claim 1 wherein removing only a first portion of a femoral head is forming a flat surface on the femoral head.

3. The method according to claim 2 wherein removing only a second portion of an acetabulum bearing surface is forming a flat surface on the acetabulum.

4. The method according to claim 1 wherein the first prosthetic device defines a first device bearing surface that is configured to engage a second device bearing surface of the second prosthetic.

5. The method according to claim 4 wherein the first device bearing surface is configured to interface with the non-removed bearing portion of the acetabulum.

6. The method according to claim 1 wherein the non-removed bearing portion of the head is a bearing surface.

7. The method according to claim 1 wherein the first and second prosthetic devices have generally parallel coupling surfaces.

8. A method for implanting a joint prosthesis into a hip joint, the method comprising:
   minimally distracting a femoral head from an acetabular socket of the joint to place the joint into a minimally distracted position;
   forming a first flat surface on only a portion of a bearing surface of the femoral head while the joint is in the minimally distracted position;
   forming a second flat surface on only a portion of an acetabulum bearing surface while the joint is in the minimally distracted position;
   implanting a first prosthetic device onto the first flat surface, while the joint is in the minimally distracted position, the first prosthetic being positioned to place a first articulating prosthetic bearing surface flush with a non-removed articulating bearing portion of the femoral head; and
   implanting a second prosthetic device onto the second flat surface, while the joint is in the minimally distracted position, the second prosthetic being positioned to place a second articulating bearing surface of the second prosthetic flush with a non-removed articulating bearing portion of the acetabulum.

9. The method according to claim 8 wherein the first prosthetic device defines a first device bearing surface that is configured to engage a second device bearing surface of the second prosthetic.

10. The method according to claim 9 wherein the second device bearing surface is configured to interface with the non-removed bearing portion of the femoral head.

11. The method according to claim 8 wherein the portion of the bearing surface of the femoral head comprises defective tissue.

12. The method according to claim 8 wherein forming a first flat surface and forming a second flat surface is forming a pair of generally parallel flat surfaces.

13. The method according to claim 8 wherein implanting a first prosthetic device is implanting a first prosthetic device having a first flat interface surface onto the first flat surface.

14. The method according to claim 8 wherein implanting a second prosthetic device is implanting a second prosthetic device having a second flat interface surface onto the second flat surface.

15. The method according to claim 8 wherein implanting a first prosthetic device is coupling the first prosthetic device to the first flat surface using at least one of a screw, a stem or bone cement.

16. The method according to claim 8 wherein forming a first flat surface is resecting a portion of the head using at least one of a reamer and a cutting blade.

17. A method for implanting a joint prosthesis into a hip joint, the method comprising:
    removing only a first portion of a femoral head while the joint is in a non-distracted position;
    removing only a second portion of an acetabulum while the joint is in a non-distracted position;
    implanting a means for resurfacing only a portion of the femoral head while the joint is in a non-distracted position, the means for resurfacing only a portion of the femoral head being positioned to place a first articulating bearing surface flush with a non-removed articulating bearing surface of the femoral head; and
    implanting a means for resurfacing only a portion of the acetabulum while the joint is in a non-distracted position, the means for resurfacing only a portion of the acetabulum being positioned to place a second articulating bearing surface flush with a non-removed articulating bearing portion of the acetabulum.

18. The method according to claim 17 wherein removing only a first portion of a femoral head is forming a flat surface on the femoral head.

19. The method according to claim 17 wherein implanting a means for resurfacing only a portion of the acetabulum bearing surface is coupling the means for resurfacing only a portion of the acetabulum bearing surface to acetabulum using at least one of a screw, a stem or bone cement.

20. The method according to claim 17 wherein removing only a first portion of the femoral head is forming a pair of intersecting cuts in the femoral head.

* * * * *